(12) United States Patent
Uraki et al.

(10) Patent No.: US 8,911,976 B2
(45) Date of Patent: Dec. 16, 2014

(54) LIGNIN-BASED ENZYME STABILIZER

(75) Inventors: Yasumitsu Uraki, Hokkaido (JP);
Harumi Honma, Hokkaido (JP);
Tatsuhiko Yamada, Ibaraki (JP);
Satoshi Kubo, Ibaraki (JP); Masanobu Nojiri, Ibaraki (JP)

(73) Assignee: Forestry and Forest Products Research Institute, Tsukuba-shi (JP)

( * ) Notice: Subject to any disclaimer, the term of this patent is extended or adjusted under 35 U.S.C. 154(b) by 124 days.

(21) Appl. No.: 13/583,479

(22) PCT Filed: Mar. 7, 2011

(86) PCT No.: PCT/JP2011/055267
§ 371 (c)(1),
(2), (4) Date: Sep. 7, 2012

(87) PCT Pub. No.: WO2011/111664
PCT Pub. Date: Sep. 15, 2011

(65) Prior Publication Data
US 2012/0329100 A1 Dec. 27, 2012

(30) Foreign Application Priority Data

Mar. 8, 2010 (JP) ................. 2010-050596

(51) Int. Cl.
*C12N 9/96* (2006.01)
*C12P 7/14* (2006.01)
*C12P 19/14* (2006.01)
*C07G 1/00* (2011.01)
*C08H 7/00* (2011.01)
*C12N 1/22* (2006.01)
*C12P 7/10* (2006.01)

(52) U.S. Cl.
CPC .. *C07G 1/00* (2013.01); *C08H 6/00* (2013.01);
*C12N 1/22* (2013.01); *C12N 9/96* (2013.01);
*C12P 7/10* (2013.01); *Y02E 50/16* (2013.01)
USPC ............................. 435/99; 435/162; 435/188

(58) Field of Classification Search
CPC .............. C07G 1/00; C08H 6/00; C12N 1/22;
C12N 9/96; C12P 7/00
USPC .......................................... 435/99, 162, 188
See application file for complete search history.

(56) References Cited

FOREIGN PATENT DOCUMENTS

JP 2008 92910 4/2008

OTHER PUBLICATIONS

Uraki, Y., et al., "Preparation of amphiphilic lignin derivative as a cellulase stabilizer," The Japan Wood Research Society, vol. 47, No. 4, pp. 301 to 307, (2001).
Ooshima, H., et al., "Adsorption of Cellulase from Trichoderma reesei on Cellulose and Lignacious Residue in Wood Pretreated by Dilute Sulfuric Acid with Explosive Decompression," Biotechnol. Bioeng., vol. 36, No. 5, pp. 446 to 452, (1990).
International Search Report Issued May 17, 2011 in PCT/JP11/055267 Filed Mar. 7, 2011.
International Preliminary Report on Patentability in international application No. PCT/JP2011/055267, issued on Oct. 2, 2012.

*Primary Examiner* — Chih-Min Kam
(74) *Attorney, Agent, or Firm* — Oblon, Spivak, McClelland, Maier & Neustadt, L.L.P.

(57) ABSTRACT

The invention relates to an enzyme stabilizer comprising a lignin derivative produced by reaction between lignin and a hydrophilic compound, and to a method of saccharifying lignocellulosic biomass which employs the enzyme stabilizer. According to the invention it is possible to accomplish effective saccharification of cellulosic biomass with saccharifying enzymes, by enhancing saccharifying enzyme activity and preventing nonspecific adsorption of saccharifying enzyme onto substrate.

10 Claims, 1 Drawing Sheet

Lignin-based enzyme stabilizer addition % (with respect to biomass)

Lignin-based enzyme stabilizer addition % (with respect to biomass)

LIGNIN-BASED ENZYME STABILIZER

CONTINUING APPLICATION INFORMATION

The present application is National Stage of international application no. PCT/JP2011/055267, filed on Mar. 7, 2011.

TECHNICAL FIELD

The present invention relates to a saccharifying enzyme stabilizer, and to a method of saccharifying cellulosic biomass using the saccharifying enzyme stabilizer.

BACKGROUND ART

Production of ethanol obtainable using biomass starting materials (bioethanol) is increasing in importance as a means of obtaining renewable liquid fuel, and bioethanol production is being researched not only from edible resources such as starch, but also from lignocellulosic biomass such as wood. When lignocellulosic biomass such as wood is used, the traditional method has been researched to decompose the cellulose in the biomass into monosaccharides with concentrated sulfuric acid and then perform fermentation. However, this method has not been widely adopted because of the difficulty of establishing and managing acid resistance of the apparatuses used to handle the concentrated sulfuric acid, and efficient techniques for recovery of the sulfuric acid.

Other methods have also been investigated, that do not use acids such as sulfuric acid but rather make use of enzymes such as cellulases for monosaccharification of the polysaccharide components of biomass (saccharification), and accomplish ethanol fermentation using yeasts and the like (enzymatic saccharification and fermentation methods). However, when such methods are applied to lignocellulosic biomass such as wood, some sort of treatment (pretreatment) is required before the enzyme saccharification.

The pretreatment for enzyme saccharification is a step in which the cellulose and other materials in the biomass are converted to a state that allows effective action by the enzymes, and it may involve physical or chemical treatment. The physical treatment often involves milling with a ball mill or the like. Chemical treatment involves removal of lignin with chemical agents to obtain cellulose, as in the chemical steps for producing wood pulp. PTL 1, for example, discloses that efficient production of bioethanol can be accomplished by pretreatment of the biomass by alkaline cooking or kraft cooking to remove most of the lignin in the biomass, followed by enzyme saccharification and fermentation.

CITATION LIST

Patent Literature

[PTL 1] Japanese Unexamined Patent Application Publication No. 2008-92910

SUMMARY OF INVENTION

Technical Problem to be Solved by Invention

In enzyme saccharification and fermentation methods, however, a portion of the loaded enzyme usually becomes adsorbed onto the biomass substrate and can no longer contribute to saccharification, and therefore the enzyme activity is reduced. The enzyme activity is especially reduced when the enzyme is adsorbed onto lignin rather than other biomass components. Reutilization of the enzymes is generally difficult. Cost reduction for enzymes is considered important in industry, and a key point for the practical implementation of these technologies is to establish an efficient method of using the enzymes.

Lignin has very high adsorption power for enzymes, and therefore its removal is advantageous for enzyme saccharification. The technique described in PTL 1 involves removing most of the lignin by chemical treatment before enzyme saccharification, but it is difficult to separate all of the lignin from biomass.

Yet lignin, as one of the three main components of biomass, is an organic compound that is the second most abundantly accumulated on the earth. It is separated in chemical pulping processes and bioethanol pretreatment processes and created as a by-product in wood pulp and bioethanol production, but there are few methods for its effective reutilization other than as a heat source, and therefore effective utilization methods for it have been sought.

It is an object of the present invention, which has been accomplished in light of these circumstances, to accomplish effective saccharification of cellulosic biomass with saccharifying enzymes, by increasing saccharifying enzyme activity and preventing nonspecific adsorption of saccharifying enzymes onto the substrate.

Solution to Problem

As a result of much research, the present inventors have completed this invention upon finding that saccharifying enzyme activity is increased and nonspecific adsorption of saccharifying enzymes onto substrate is significantly reduced by using a lignin derivative produced by reaction between lignin and a hydrophilic compound as an enzyme stabilizer.

Specifically, the invention provides an enzyme stabilizer comprising a lignin derivative produced by reaction between lignin and a hydrophilic compound. The enzyme stabilizer can prevent inactivation of enzymes and stabilize enzyme activity.

According to the invention there is provided a method for stabilizing an enzyme, comprising adding a lignin derivative produced by reaction between lignin and a hydrophilic compound to a reaction system comprising a substrate and an enzyme. The method can prevent inactivation of enzymes and stabilize enzyme activity.

There is also provided according to the invention a method of saccharifying lignocellulosic biomass using an enzyme, comprising adding the aforementioned enzyme stabilizer to a fermentation system. According to this saccharifying method it is possible to reutilize enzyme or reduce the amount of enzyme used.

Advantageous Effects of Invention

The enzyme stabilizer and enzyme stabilizing method of the invention significantly can inhibit adsorption of an enzyme onto biomass components, and can prevent inactivation of the enzyme. By the saccharifying method of the invention it is also possible to reutilize enzyme or reduce the amount of enzyme used. In addition, since there is no limitation on the type of lignin starting material for production of the enzyme stabilizer of the invention, and many different types of lignin may be used such as those are by-products of wood pulping technology and bioethanol production, this contributes to the overall utilization of biomass.

DESCRIPTION OF EMBODIMENTS

Explanation of Terms

Figure 1:
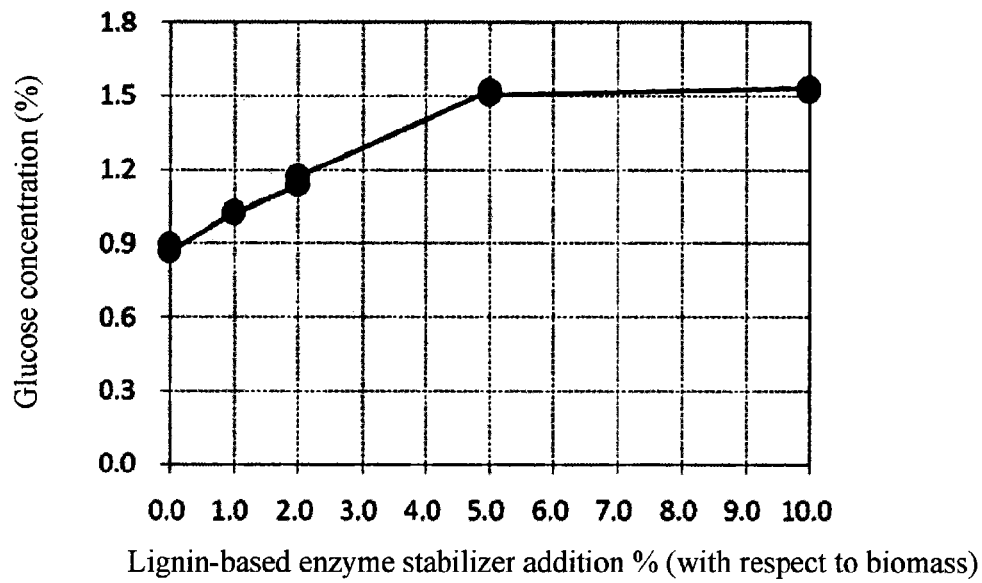
FIG. 1 is a graph showing the effect of a lignin-based enzyme stabilizer on glucose production volume in an enzyme saccharification step.

The meanings of the terms used throughout the present specification and the claims will now be defined.
(1) Enzyme Stabilization As used herein, the term "enzyme stabilization" refers to, in the context of reaction between a substrate and enzyme, preventing inactivation of the enzyme and stabilizing the enzyme activity, by the presence of an enzyme stabilizer. Specifically, the residual enzyme activity is maintained at 30% or greater, preferably 50% or greater and more preferably 70% or greater, compared to using no enzyme stabilizer, under the enzyme saccharification reaction conditions of Test Example 1 described below. The method of measuring the enzyme activity may be the method described in the present specification, or a method described in a commercial product catalog or in the literature, employed as appropriate by a person skilled in the art.
(2) Enzyme The term "enzyme" as used herein refers to a macromolecular compound mainly comprised of a protein and catalyzing a chemical reaction, and especially a saccharifying enzyme. The saccharifying enzyme may be a cellulase that decomposes cellulose, a hemicellulase that decomposes hemicellulose, a glucosidase (β-glucosidase), or an amylase that decomposes starch, and it is preferably a cellulase.

Embodiments of the invention will now be described in detail. Description of recurring content will be appropriately omitted to avoid the complexity of repetition.

Embodiment 1

Enzyme Stabilizer

The enzyme stabilizer of this embodiment is an enzyme stabilizer comprising a lignin derivative produced by reaction between lignin and a hydrophilic compound. The examples described below demonstrate that the lignin derivative produced by reaction between lignin and a hydrophilic compound, in reaction between a substrate and an enzyme, can prevent inactivation of the enzyme and stabilize the enzyme activity. The enzyme stabilizer of this embodiment comprising a lignin derivative can therefore prevent inactivation of enzymes and stabilize enzyme activity.
(Lignin)

The lignin used as the starting material for the lignin derivative of the invention may be any type of lignin, such as kraft lignin, lignin acetate, organosolv lignin, steam explosion lignin or the like, separated from wood chips by pulping, or lignin sulfate, alkaline lignin or the like resulting as a by-product of biomass conversion techniques, but there is no limitation to the above. Lignin from any source may be used, including lignin obtained from softwoods such as cedar, cypress and pine; lignin obtained from hardwoods such as beech and oak; or lignin obtained from herbaceous plants such as rice straw, fir and bagasse, with no limitation to the above.

The lignin used for the invention can be obtained by isolation from a starting material using a method known in the technical field, such as the method described in "Lignin no Kagaku [Lignin Chemistry]" (Nakano, J., Uni Publishing).

The molecular weight of the lignin will depend on the starting material and the isolation method. The lignin used for the invention may be lignin with any molecular weight, and for example, lignin with an average molecular weight of 500 to 1,000,000 and preferably an average molecular weight of 5000 to 100,000 may be used.
(Hydrophilic Compound)

The hydrophilic compound used as a starting material for the lignin derivative of the invention is a compound containing at least one hydrophilic group such as —OH, —O— or —NH$_2$ in the molecule. Preferably, the hydrophilic compound is a compound represented by the following formula (I):

$$R^1-C_mH_{2m}-(C_nH_{2n}O)_p-C_qH_{2q}-R^2 \tag{I}$$

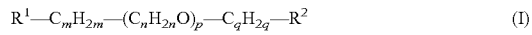

wherein $R^1$ and $R^2$ each independently are hydrogen, an OH, methyl, glycidyl or glycidyl ether group, m is 0 to 20, n is 2 to 4, p is 1 to 30, q is 0 to 20, and the carbon atoms of the alkylene units may each have 1 or 2 substituents independently selected from among alkyl, —OH, —NH$_2$, glycidyl and glycidyl ether groups, wherein —(C$_n$H$_{2n}$O)$_p$— may be mixed alkoxide units, in which case the alkoxide units may be in any optional sequence.

Examples of hydrophilic compounds to be used for the invention include the following compounds, with no particular limitation thereto:

glycol-based compounds such as ethylene glycol, diethylene glycol, polyethylene glycols of various molecular weights, propylene glycol, polypropylene glycols of various molecular weights, glycerin and polyglycerins of various molecular weights;

glycidyl ether-based compounds such as methyl glycidyl ether, ethyl glycidyl ether, propyl glycidyl ether, 2-ethylhexyl glycidyl ether, decyl glycidyl ether, stearyl glycidyl ether, polyethylene glycol-monoethyl-glycidyl ether, polyethylene glycol-monomethyl-glycidyl ether, lauryl alcohol-polyethylene oxide-glycidyl ether, ethylene glycol-diglycidyl ether, poly(ethylene glycol)diglycidyl ether (n'=1-30 and preferably 9-30), propyleneglycol diglycidyl ether, poly(propylene glycol)diglycidyl ether (n'=1-30 and preferably 9-30), neopentyl glycol diglycidyl ether, 1,3-propanediol diglycidyl ether, 1,4-butanediol diglycidyl ether, 1,5-pentanediol diglycidyl ether, 1,6-hexanediol diglycidyl ether, 1,4-cyclohexanedimethanol diglycidyl ether, 1,4-cyclohexanediol diglycidyl ether, 1,3-cyclohexanediol diglycidyl ether, glycerol diglycidyl ether, pentaerythritol diglycidyl ether, sorbitol diglycidyl ether, glycerol triglycidyl ether, diglycerol polyglycidyl ether, polyglycerol polyglycidyl ether, sorbitol polyglycidyl ether, tertiary glycidyl carboxylate ester, 1,1,1-tris (hydroxymethyl)ethane-triglycidyl ether, 1,1,1-tris (hydroxymethyl)ethane-diglycidyl ether, trimethylolpropane-diglycidyl ether, trimethylolpropane-triglycidyl ether, phloroglucinol triglycidyl ether, pyrogallol triglycidyl ether, triglycidyl ether cyanurate, pentaerythritol tetraglycidyl ether, sorbitol tetraglycidyl ether, and these compounds with reduced glycidyl ether group functionality by reaction of the glycidyl groups with alkoxides such as methoxy and ethoxy.

These hydrophilic compounds may be commercially available products, or compounds prepared by methods known in the art. These specified hydrophilic compounds are included among the compounds represented by formula (I) above.

The lignin derivative of the invention may be prepared with selection of any of these hydrophilic compounds to control the performance of the obtained enzyme stabilizer.

Preferred hydrophilic compounds are glycidyl ether-based compounds and glycol-based compounds. Specific preferred examples of hydrophilic compounds are selected from among polyethylene glycol-monoethyl-glycidyl ether, polyethylene glycol-monomethyl-glycidyl ether and lauryl alcohol-polyethylene oxide-glycidyl ether.

According to a more preferred embodiment of the invention, the hydrophilic compound is lauryl alcohol-polyethylene oxide-glycidyl ether. Using such a hydrophilic compound is preferred as it will result in more excellent performance of the obtained lignin derivative as an enzyme stabilizer.

According to a preferred embodiment of the invention, the hydrophilic compound is lauryl alcohol-polyethylene oxide-glycidyl ether having 5 to 15 repeating units of ethylene oxide.

(Lignin Derivative)

The lignin and hydrophilic compound may be reacted to introduce hydrophilic groups into the hydrophobic lignin, to obtain an amphiphilic lignin derivative for the invention. The method for introducing hydrophilic groups into the lignin may be a known method for reacting reactive groups in hydrophilic compounds with hydroxyl groups in lignins.

The amount of hydrophilic compound reacted with the lignin in the reaction of the invention may be set according to the type of lignin and hydrophilic compound used, and the performance desired for the enzyme stabilizer. The amount of hydrophilic compound to be added is calculated based on the number of hydroxyl groups in the lignin that is used and the number of glycidyl or hydroxyl groups in the hydrophilic compound. Theoretically, all of the hydroxyl groups in the lignin can potentially react with the glycidyl or hydroxyl groups in the hydrophilic compound. There is no limit on the amount of hydrophilic compound used, and usually, the amount of the glycidyl-based compound is 5-100 parts by weight with respect to 10 parts by weight of the lignin, preferably 10-60 parts by weight with respect to 10 parts by weight of the lignin, and more preferably 30-40 parts by weight with respect to 10 parts by weight of the lignin.

According to a preferred mode, the lignin derivative of the invention may be produced by reacting the lignin and hydrophilic compound under alkaline conditions. Since there is no limitation on the type of lignin starting material used for production of the lignin derivative in this production method, and many different types of lignin may be used that are by-products of wood pulping technology and bioethanol production, this contributes to the overall utilization of biomass.

When a glycidyl ether-based compound is used as the hydrophilic compound, the lignin is dissolved in an aqueous alkali solution, and the hydroxyl groups in the lignin (lignin-OH) that has been freed under the alkaline conditions are reacted with the glycidyl groups in the glycidyl ether-based compound to produce a lignin derivative. Black liquor obtained after alkaline cooking of the lignocellulosic biomass may be used as the aqueous alkali solution of lignin.

The reaction temperature is not particularly restricted, and will usually be 50° C. to 100° C., and is preferably 70° C.

The reaction time is also not particularly restricted, and will usually be 30 minutes to 24 hours, and is preferably 1 hour to 12 hours and more preferably 3 hours to 6 hours.

For the reaction of the invention, sodium hydroxide, potassium hydroxide, calcium hydroxide, magnesium hydroxide, lithium hydroxide or the like may be used to produce the alkaline conditions.

Upon completion of the reaction between the lignin and glycidyl-based compound, an acid is added to the reaction system for neutralization. The acid to be added may be any acid so long as it does not have an adverse effect, and for example, an inorganic acid such as hydrochloric acid, phosphoric acid or sulfuric acid or an organic acid such as formic acid or acetic acid may be used.

The reaction is complete when the obtained lignin derivative has become hydrophilic by introduction of the hydrophilic compound into the hydrophobic lignin. Completion of the reaction between the lignin and hydrophilic compound can be judged, for example, by adding an acid to a sampled portion of the reaction solution and determining whether or not the lowered pH produces a precipitate. If the reaction is incomplete, unreacted lignin will be deposited as a precipitate. If the reaction is complete, no precipitate will be produced, signifying that the amphiphilic lignin derivative has been obtained.

According to one embodiment of the invention, lignin is dissolved in an aqueous solution of sodium hydroxide, the obtained aqueous alkali solution of lignin is heated to about 70° C. under ordinary pressure, a prescribed amount of a glycidyl ether-based compound is added, and reaction is conducted for approximately 3 hours while stirring, and then upon completion of the reaction, an acid is added to the reaction system for neutralization, to obtain the lignin derivative.

When a glycol-based compound is used as the hydrophilic compound, an acid catalyst may be added to a mixture of the lignin and glycol-based compound for reaction to prepare a lignin derivative.

The acid catalyst used may be hydrochloric acid, sulfuric acid or the like. The amount of the acid catalyst to be added will usually be 0.1-3.0 wt % with respect to the glycol-based compound.

The reaction temperature is not particularly restricted, and will usually be 100° C. to 200° C., preferably 120° C. to 160° C. and more preferably 140° C.

The reaction time is also not particularly restricted, and will usually be 30 minutes to 180 minutes, preferably 60 minutes to 120 minutes, and more preferably 90 minutes.

For this reaction, water is preferably added to the reaction system after complete reaction between the lignin and glycol-based compound, to remove the non-water-soluble components.

The lignin derivative obtained by the reaction may be used directly as an enzyme stabilizer, or if necessary, it may be subjected to ultrafiltration for desalting and to remove the unreacted hydrophilic compound. For example, an ultrafiltration device that can eliminate molecular weights of 3000 and smaller is preferably used for the filtration.

The lignin derivative obtained by the reaction may also, if necessary, be thoroughly dried by a drying method employed in the art, such as freeze-drying.

(Enzyme Stabilizer)

When the lignin derivative of the invention is to be used as an enzyme stabilizer, it may be used in the form of an aqueous solution or in dry powdered form.

The enzyme stabilizer of the invention may contain any optional additives as well, in ranges that do not interfere with the performance. Examples of such additives include pH regulators, antioxidants, water-soluble or water-insoluble carriers, dispersing agents, and water-soluble metal inorganic or organic acid salts.

Embodiment 2

Enzyme Stabilizing Method

The enzyme stabilizing method of this embodiment is a method for stabilizing an enzyme, comprising adding a lignin derivative produced by reaction between lignin and a hydrophilic compound to a reaction system comprising a substrate and an enzyme. The examples described below demonstrate that the lignin derivative produced by reaction between lignin and a hydrophilic compound, in reaction between a substrate and an enzyme, can prevent inactivation of the enzyme and stabilize the enzyme activity. The enzyme stabilizing method of this embodiment, which employs the lignin derivative described above, can prevent inactivation of enzymes and stabilize enzyme activity.

The lignin derivative used in the enzyme stabilizing method of this embodiment basically has the same construction and effect as the lignin derivative used in the enzyme stabilizer explained in detail for Embodiment 1. Explanation of the aspects similar to Embodiment 1 will therefore be optionally omitted.

The enzyme for the enzyme reaction is preferably a saccharifying enzyme, and most preferably a cellulase. The substance for the enzyme reaction is preferably cellulose, and most preferably lignocellulose derived from wood or the like.

The lignin derivative may be added in any desired amount for use in the enzyme stabilizing method of this embodiment, and for example, it may be added at 0.5-20.0 wt %, preferably 1-15 wt % and more preferably 9-10 wt % with respect to the substance (for example, lignocellulosic biomass), in terms of solid weight. Addition in this range is preferred because it can prevent inactivation of the enzyme and further stabilize the enzyme activity.

Embodiment 3

Enzyme Saccharification Method

The enzyme saccharification method of this embodiment is a method of saccharifying lignocellulosic biomass using an enzyme, comprising adding an enzyme stabilizer according to Embodiment 1. The enzyme stabilizer used for this embodiment can prevent inactivation of the enzyme and stabilize the enzyme activity as mentioned above. In a saccharifying method using the enzyme stabilizer, therefore, it is possible to reutilize the enzyme or reduce the amount of enzyme used.

The phrase "method of saccharifying lignocellulosic biomass using an enzyme (saccharifying method of lignocellulosic biomass using an enzyme)", as used herein, refers to any method that accomplishes saccharification of lignocellulosic biomass with an enzyme, and for example, it may refer to the saccharifying method (method for producing ethanol) described in Japanese Unexamined Patent Application Publication No. 2008-92910. The content of Japanese Unexamined Patent Application Publication No. 2008-92910 is incorporated herein by reference.

The enzyme saccharification method of this embodiment comprises:

(a) undergoing delignification of lignocellulosic biomass by alkaline cooking, (b) culturing a microorganism for producing saccharifying enzyme using the alkaline cooked lignocellulosic biomass as a carbon source, to produce an enzyme suitable for saccharifying lignocellulosic biomass, and (c) adding the obtained culture solution containing the saccharifying enzyme, with an ethanol fermentation microorganism and the enzyme stabilizer of the invention, to alkaline cooked lignocellulosic biomass, and conducting fermentation in the presence of the enzyme stabilizer.

In order to obtain a saccharifying enzyme suitable for saccharifying lignocellulosic biomass according to the invention, microorganisms for producing saccharifying enzymes are first cultured using an alkaline cooked product of lignocellulosic biomass as the carbon source.

The alkaline cooking method may be a soda method or kraft method.

A soda method is a method for removal of lignin from lignocellulosic biomass using an alkali agent such as sodium hydroxide, potassium hydroxide or sodium carbonate, and additives such as quinone-based digesting aids, oxygen, hydrogen peroxide and polysulfide may be used.

A kraft method is a method for removal of lignin from lignocellulosic biomass using an alkali agent such as sodium hydroxide, potassium hydroxide or sodium carbonate, in combination with a sulfur-containing chemical such as sodium sulfide or sodium sulfite, and additives such as quinone-based digesting aids, oxygen, hydrogen peroxide and polysulfide may be used.

The chemical to be used for alkaline cooking may be sodium hydroxide, potassium hydroxide or sodium carbonate, and the additives may be sodium sulfide, a quinone-based digesting aid, oxygen, hydrogen peroxide and polysulfide. The alkali agent is added at 5-40% of the dry weight of the lignocellulosic biomass to be used for cooking. The additives such as the quinone-based digesting aid, oxygen, hydrogen peroxide and polysulfide may be selected depending on the properties and amount of the lignin contained in the lignocellulosic biomass, and they do not need to be used if cooking can be accomplished with the alkali agent alone. When added, additives are preferably used at no greater than 10% of the weight of the lignocellulosic biomass to be used for cooking. In order to promote cooking, the lignocellulosic biomass to be used in alkaline cooking may be pulverized or cut or fragmented into chips beforehand. Adjustment may be made to the alkaline cooking condition: the weight concentration of the lignocellulosic biomass during alkaline cooking of 5 to 50%, the reaction temperature of 100° C. to 200° C. and preferably 140° C. or higher, and the heating time of 60 minutes to 500 minutes, as suitable for the chip shapes and dimensions and the quality and amount of the lignin contained.

After thermal reaction, the alkali is removed and the cooked biomass is rinsed and dewatered. The rinsing is performed to a pH that does not inhibit the subsequent saccharification and fermentation step, and preferably to a pH of no greater than 9. The recovered alkaline waste liquid contains lignin, and it may be combusted with a recovery boiler to recover the heat and salvage the soda ash for reutilization. The obtained heat can be reused in the production process, thus allowing cost to be reduced. If the rinsing and dewatering treatments are carried out under aseptic conditions, the sterilization step before fermentation may be omitted.

For use as a starting material for production of a saccharifying enzyme and for ethanol production as described below, the water is removed from the lignocellulosic biomass treated by the aforementioned series of steps, with control to a moisture content of 20-90% and preferably 40-80%, avoiding thorough drying.

Examples of microorganisms for producing saccharifying enzyme to be used for the invention include strains belonging to the aerobic genera *Trichoderma, Aspergillus, Humicola, Irpex* and *Acremonium*. The liquid medium used for culturing may one that is suitable for culturing of microorganisms for producing saccharifying enzyme, comprising 0.5-10 wt % alkaline cooked lignocellulosic biomass as the sole carbon source, a nitrogen source such as yeast extract or peptone, and salts and the like. The culturing temperature may also be modified according to the nature of the microorganisms for producing saccharifying enzyme. The culturing period is up to the saturation of enzyme activity, using cellulase activity in the culture solution as the indicator.

The culture solution of the microorganism for producing saccharifying enzyme that has been obtained by culturing can be used directly without treatment as a saccharifying enzyme for alkaline cooked lignocellulosic biomass, and it is therefore advantageous toward reducing cost for industrial production of alcohols.

The culture solution of the microorganism for producing saccharifying enzyme and alcohol fermentation microorganisms are added to alkaline cooked lignocellulosic biomass for saccharification and fermentation to produce ethanol. It is a feature of the invention that the enzyme stabilizer of the invention is further added and fermentation is conducted in the presence of the enzyme stabilizer.

The enzyme stabilizer used in the saccharifying method of this embodiment basically has the same construction and effect as the enzyme stabilizer described in detail for Embodiment 1. Explanation of the aspects similar to Embodiment 1 will therefore be optionally omitted.

The enzyme stabilizer to be used in the saccharifying method of this embodiment can be produced using as the starting material lignin in the alkaline waste liquid recovered after alkaline cooking. In other words, black liquor obtained after alkaline cooking of lignocellulosic biomass may be used as an aqueous alkali solution of the lignin. This is preferred as it allows comprehensive reuse of the lignocellulosic biomass.

The enzyme stabilizer to be used in the saccharifying method of this embodiment may be added in any desired amount, and for example, it may be added at 0.5-20.0 mass %, preferably 1-15 mass % and more preferably 9-10 mass % with respect to the lignocellulosic biomass as the starting substrate, as solid weight. This amount of addition is preferred as it can minimize adsorption of the enzyme onto the biomass components, and increase the enzyme activity.

The saccharifying enzyme used for the invention may be any desired enzyme that has cellulase, hemicellulase or β-glucosidase activity. Examples of such microorganisms for producing saccharifying enzyme include strains belonging to the aerobic genera *Trichoderma, Aspergillus, Humicola, Irpex* and *Acremonium*.

The lignocellulosic biomass is preferably pretreated before saccharification with the enzyme. The pretreatment is a step in which the cellulose and other materials in the biomass are converted to a state that allows effective action by the enzymes, and it may involve physical or chemical treatment. Physical treatment may be milling with a ball mill or the like. Chemical treatment may be treatment in which the lignin in the biomass is removed with a chemical agent to obtain cellulose, such as alkaline cooking, kraft cooking, organosolv cooking or the like.

In one embodiment of the invention, an ethanol fermentation microorganism is added together with the saccharifying enzyme to allow continuous and simultaneous saccharification and fermentation. The ethanol fermentation microorganism may be one belonging to the genus *Saccharomyces, Zymomonas, Pichia* or the like. A gene recombinant strain may also be used so long as it is capable of alcohol fermentation. Preferably, the ethanol fermentation microorganism is cultured in a liquid medium before ethanol fermentation, to increase the cell count.

The amount of saccharifying enzyme added for saccharification is adjusted for 5-50 units of cellulase activity per gram of cellulose in the lignocellulosic biomass that is used as the starting substrate.

A larger loading amount of ethanol fermentation microorganism will give greater fermentation efficiency, and preferably an amount of microorganism is ensured that will allow the sugars produced by the saccharification to be simultaneously and completely converted to ethanol.

High efficiency is obtained with saccharification/fermentation in which the saccharification and ethanol fermentation are conducted simultaneously. The saccharification may instead be carried out first and the saccharified solution subsequently fermented.

Simultaneous saccharification/fermentation may be accomplished either with a system in which the saccharification and fermentation are carried out in the same reactor, or with a system in which the saccharification and fermentation are carried out in separate reactors.

When the saccharification and fermentation are carried out in the same reactor, the pH and temperature of the reaction mixture are selected so that both saccharification and fermentation can take place. The conditions are preferably closer to fermentation conditions for the ethanol fermentation microorganism, with a pH of 4 to 7 and a temperature of 20° C. to 40° C. If simultaneous saccharification/fermentation is carried out under anaerobic conditions, it will be possible to inhibit proliferation of the microorganisms for producing saccharifying enzyme, which are aerobic, and to minimize consumption of sugar that occurs when the microorganisms for producing saccharifying enzyme proliferate. In addition, stirring in the simultaneous saccharification/fermentation will help promote saccharification and improve the ethanol yield. Simultaneous saccharification/fermentation may also be carried out while separating and recovering the ethanol product. This system accomplishes the entire saccharification and ethanol fermentation in a single reactor and therefore simplifies the production process.

In a system where the saccharification and fermentation are simultaneously carried out in separate reactors, the saccharification is conducted at a temperature suitable for saccharification. The temperature is preferably 40° C. to 60° C. The pH of the reaction mixture is preferably 4 to 6, equal to the fermentation conditions. The saccharified solution is continuously removed and supplied to a fermenter. The ethanol fermentation microorganisms in the fermenter do not need to be, but are preferably, immobilized. The preferred fermentation conditions are a pH of 4 to 7 and a temperature of 20° C. to 40° C. The ethanol fermentate is recirculated for saccharification, and saccharification and fermentation are carried out simultaneously. The ethanol produced may then be separated and recovered.

In a system where saccharification is carried out first and then the saccharified solution is fermented, the saccharification is carried out at a temperature suitable for saccharification. The temperature is preferably 40° C. to 60° C. The pH of the reaction mixture is preferably 4 to 7, for conditions suitable for saccharification. Upon completion of saccharification, the saccharified solution is removed and supplied to a fermenter. The ethanol fermentation microorganisms in the fermenter do not need to be, but are preferably, immobilized. The fermentation conditions are selected so as to be suitable for ethanol fermentation. Preferably, the pH is 4 to 8 and the temperature is 20° C. to 40° C. The ethanol produced during ethanol fermentation may then be separated and recovered.

The lignocellulosic biomass as the substrate for saccharification may be at least one type selected from the group consisting of arboreous plants, herbaceous plants, their processed products and their waste products. For efficient alkaline cooking, however, it is preferably a product that has been finely pulverized.

Examples of arboreous plants for the invention include cedar, cypress, larch, pine, Douglas fir, western red cedar, hemlock, poplar, white birch, willow, eucalyptus, sawtooth oak, red oak, kashi (bamboo leaved oak), oak chestnut, beech, acacia, bamboo, bamboo grass, oil palm, sago palm, and the like. Bark, branches, fruit clusters and fruit hulls may also be used. Processed materials including plywood, fiber board or laminated wood obtained using such materials may also be used. Used and disassembled parts from architectural structures may be utilized as well. Processed lignocellulosic biomass such as paper, or waste paper, may also be used.

Examples of herbaceous plants for the invention include rice, barley, sugarcane, common reed, Chinese silvergrass, corn, and the like.

Since the alkaline cooked lignocellulosic biomass in the reactor is decomposed and reduced in volume as saccharification proceeds, preferably fresh alkaline cooked lignocellulosic biomass is aseptically loaded into the reactor as necessary for continuous reaction.

Accumulation of ethanol in the reactor resulting in increased ethanol concentration will inhibit fermentation, and therefore the fermentation may be conducted while separating and recovering the ethanol from the fermentate. In this case, a pervaporation film or an evaporation apparatus may be employed. Operation must be at no higher than 50° C. so that the enzyme or fermentation microorganisms are not inactivated. However, this is not essential if the fermentate will not be returned to the reactor after collecting the ethanol, and operation may thus be at a temperature suitable for ethanol recovery. Moreover, since the solution after ethanol collection contains the enzyme or fermentation microorganisms, it is preferably aseptically returned to the reactor for reutilization.

Further enzyme or fermentation microorganisms may also be aseptically added as necessary.

Insoluble residue accumulates in the reactor and reduces stirring efficiency, and this may be removed with a centrifugal separator or the like. When a large amount of cellulose remains in the residue, it may be mixed with lignocellulosic biomass starting material and again subjected to alkaline cooking, or additional culture solution of the microorganisms for producing saccharifying enzyme may be further added for decomposition.

The collected ethanol may be distilled with a distilling apparatus.

EXAMPLES

The invention will now be described in greater detail by examples, with the understanding that the invention is not limited to these examples.

Example 1

Preparation of Lignin Derivative 1

To 1 kg of air-dried cedar chips there was added 6 L of an aqueous solution containing 260 g of sodium hydroxide, and then 10 g of 1,4-dihydro-9,10-dihydroxyanthracene disodium salt (anthraquinone) was added as a digesting aid, and the mixture was heated from 20° C. to 170° C. over a period of 90 minutes, and then kept at 170° C. for 150 minutes (total alkaline cooking time: 240 min). Upon completion of the reaction, the alkaline cooked cedar was removed, thoroughly washed with water, and compression-dehydrated to a moisture content of 70%. The obtained solid sample will be referred to as cedar pulp, and the reacted aqueous alkali solution as black liquor.

In order to remove the lignin eluted into the black liquor, hydrochloric acid was added to the black liquor to lower the pH to approximately 2, and lignin was deposited as a precipitate. The precipitated lignin was recovered with a centrifugal separator, thoroughly washed with distilled water and dried to obtain lignin powder. The lignin will be referred to as alkaline lignin.

A 10 g portion of the alkaline lignin was dissolved in 100 mL of a 1N sodium hydroxide aqueous solution while stirring at ordinary temperature, and then 40 g of lauryl alcohol-polyethylene oxide-glycidyl ether (DENACOL EX-171, product of Nagase ChemteX Corp.) was added as a hydrophilic compound. The solution was heated to 70° C. and stirred for 3 hours for reaction. The reaction was completed by addition of acetic acid to pH 4. An ultrafiltration device equipped with an ultrafiltration membrane for elimination of molecular weights of 1000 or smaller was used to filter the solution. After filtration, the residue was collected and freeze-dried to obtain approximately 46 g of a lignin derivative.

Example 2

Preparation of Lignin Derivative 2

(Derivatization with Glycol-Based Compound)

After adding 0.5 g of concentrated sulfuric acid to 50 g of glycerin, the mixture was thoroughly stirred at ordinary temperature and ordinary pressure for use as a glycol-based reagent. A 50 g portion of the glycol-based reagent was added to 10 g of alkaline lignin, and the mixture was heated to 150° C. while stirring under ordinary pressure. After thermal reaction for 90 minutes, the reaction layer was cooled with water. After cooling, the contents were siphoned off with a dropper and added dropwise to 1 liter of distilled water that had been vigorously agitated with a stirrer. The distilled water was filtered with a glass filter having a pore size of 16-40 μm to remove the water-insoluble portion. The obtained aqueous solution was filtered using an ultrafiltration device capable of eliminating molecular weights of 1000 or smaller. After filtration, the residue was collected and freeze-dried to obtain approximately 4 g of a lignin derivative.

The obtained lignin derivative was used as an enzyme stabilizer for the following tests.

Test Example 1

Test for Confirmation of Enzyme Inactivation-Preventing Effect

To 40 g of cedar pulp (solids: 12 g, water: 28 g) there was added 1.2 g of the lignin derivative prepared in Example 1 being 10 wt % based on the dry pulp weight, and then 560 mL of 50 mM sodium acetate buffer (pH 5) was added, and 2 mL (240 FPU) of a commercially available enzyme obtained from *Trichoderma reesei* was used as the saccharifying enzyme for enzyme saccharification while stirring at 50° C. After 48 hours of reaction, the glucose concentration was 1.5%, and 90% of the glucose in the cedar pulp was recovered as monosaccharide. The reaction mixture retained 73% activity of the loaded enzyme, thus confirming that reutilization is possible. It was thus confirmed that a lignin derivative can prevent inactivation of an enzyme by significantly minimizing adsorption of the enzyme onto substrate.

When a lignocellulosic biomass is used as a starting material for enzyme saccharification, addition of a lignin derivative as an enzyme stabilizer increased the monosaccharide yield, improved saccharifying enzyme recovery rate and lowered cost.

Test Example 2

Test for Confirmation of Enzyme Activity-Retaining Effect

Comparison was made between enzyme recovery rate and glucose production by enzyme saccharification, with different amounts of lignin derivative added between 0-10% of the dry weight of cedar pulp.

After adding 0.66 g of cedar pulp (solids: 0.2 g) to 8 mL of 50 mM acetate buffer (pH 4.5), the lignin derivative of Example 1 pre-dissolved in distilled water (0.1 g/5 mL) was added to a prescribed concentration, and then distilled water was added to a volume of 10 mL for the reaction mixture of each sample, and enzyme saccharification was conducted using 0.03 mL (4 FPU) of a commercially available enzyme from *Trichoderma reesei* as the saccharifying enzyme, while stirring at 50° C. After 48 hours of reaction, the glucose production and the remaining enzyme activity in the reaction mixture were compared.

Figure 2:
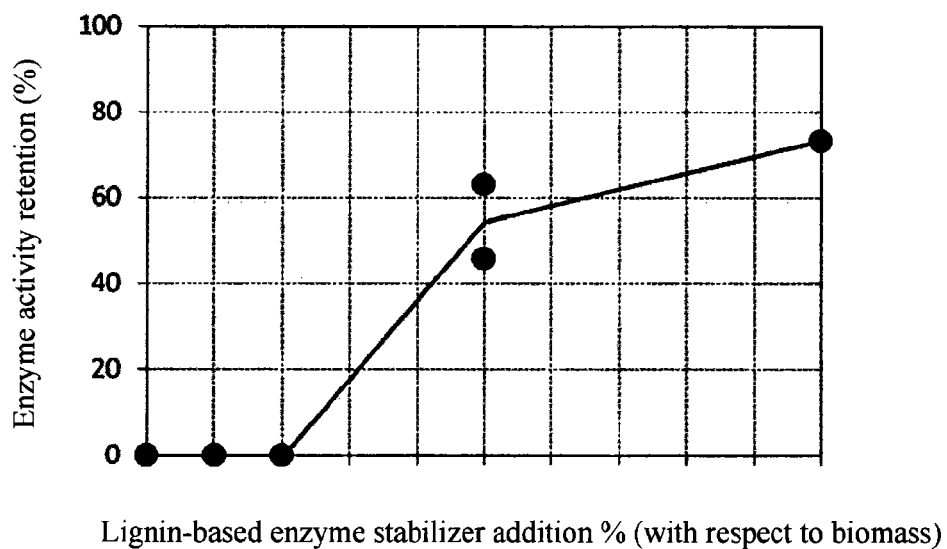
FIG. 2 is a graph showing the effect of a lignin-based enzyme stabilizer on ratio of residual enzyme activity after enzyme reaction.

The results, shown in FIG. 1, indicate that the glucose production increased with increasing lignin derivative addition, and with addition at 5% of the biomass it was possible to obtain a 1.6-fold amount of glucose compared to no addition. It was thus confirmed that a lignin derivative can increase reactivity between substrate and enzyme and enhance enzyme activity. As regards the rate of residual enzyme activity in the reaction mixture, no enzyme activity remained in the reaction mixture when no lignin derivative was added, whereas approximately 50% of the enzyme activity remained with addition at 5%, and 73% remained with addition at 10% (FIG. 2). It was thus confirmed that a lignin derivative can prevent inactivation of an enzyme by significantly minimizing adsorption of the enzyme onto substrate. This demonstrated that addition of a lignin derivative as an enzyme stabilizer increases enzyme reutilizability, allowing recovery of the enzyme after reaction, or continuous enzyme reaction by addition of more substrate.

INDUSTRIAL APPLICABILITY

The enzyme stabilizer of the invention significantly inhibits adsorption of enzymes onto biomass components, and prevents inactivation of enzymes. According to the saccharifying method of the invention it is also possible to reutilize enzyme or reduce the amount of enzyme used. In addition, since there is no limitation on the type of lignin starting material for production of the enzyme stabilizer of the invention, and many different types of lignin may be used that are by-products of wood pulping technology and bioethanol production, this contributes to the overall utilization of biomass.

The invention claimed is:

1. An enzyme stabilizer, comprising:
   a lignin derivative obtained by a process comprising reacting lignin with a hydrophilic compound, wherein the hydrophilic compound is lauryl alcohol-polyethylene oxide-glycidyl ether.

2. The stabilizer of claim 1, wherein the lignin is kraft lignin, lignin acetate, organosolv lignin, steam explosion lignin, lignin sulfate, or alkaline lignin.

3. A method for stabilizing a saccharifying enzyme, the method comprising:
   adding a lignin derivative, obtained by a process comprising reacting lignin with a hydrophilic compound in an effective amount to stabilize the saccharifying enzyme, to a reaction system comprising a substrate and a saccharifying enzyme,
   wherein the hydrophilic compound is lauryl alcohol-polyethylene oxide-glycidyl ether.

4. The method of claim 3, wherein the lignin is kraft lignin, lignin acetate, organosolv lignin, steam explosion lignin, lignin sulfate, or alkaline lignin.

5. A method of saccharifying lignocellulosic biomass with an enzyme, comprising:
   delignifying the lignocellulosic biomass by alkaline cooking, to obtain an alkaline cooked lignocellulosic biomass,
   culturing a microorganism capable of producing a saccharifying enzyme, with the alkaline cooked lignocellulosic biomass as a carbon source, to produce an enzyme suitable for saccharifying lignocellulosic biomass, and
   combining a culture solution, comprising the enzyme suitable for saccharifying lignocellulosic biomass, with an ethanol fermentation microorganism, an enzyme stabilizer comprising a lignin derivative, obtained by a process comprising reacting lignin with a hydrophilic compound in an effective amount to stabilize the enzyme, and the alkaline cooked lignocellulosic biomass, and
   fermenting in the presence of the enzyme stabilizer,
   wherein the hydrophilic compound is a glycidyl ether-based compound selected from the group consisting of methyl glycidyl ether, ethyl glycidyl ether, propyl glycidyl ether, 2-ethylhexyl glycidyl ether, decyl glycidyl ether, stearyl glycidyl ether, polyethylene glycol-monoethyl-glycidyl ether, polyethylene glycol-monomethyl-glycidyl ether, lauryl alcohol-polyethylene oxide-glycidyl ether, ethylene glycol-diglycidyl ether, poly(ethylene glycol)diglycidyl ether, propyleneglycol diglycidyl ether, poly(propylene glycol)diglycidyl ether, neopentyl glycol diglycidyl ether, 1,3-propanediol diglycidyl ether, 1,4-butanediol diglycidyl ether, 1,5-pentanediol diglycidyl ether, 1,6-hexanediol diglycidyl ether, 1,4-cyclohexanedimethanol diglycidyl ether, 1,4-cyclohexanediol diglycidyl ether, 1,3-cyclohexanediol diglycidyl ether, glycerol diglycidyl ether, pentaerythritol diglycidyl ether, sorbitol diglycidyl ether, glycerol triglycidyl ether, diglycerol polyglycidyl ether, polyglycerol polyglycidyl ether, sorbitol polyglycidyl ether, tertiary glycidyl carboxylate ester, 1,1,1-tris(hydroxymethyl)ethane-triglycidyl ether, 1,1,1-tris(hydroxymethyl)ethane-diglycidyl ether, trimethylolpropane-diglycidyl ether, trimethylolpropane-triglycidyl ether, phloroglucinol triglycidyl ether, pyrogallol triglycidyl ether, triglycidyl ether cyanurate, pentaerythritol tetraglycidyl ether, sorbitol tetraglycidyl ether, and these compounds with reduced glycidyl ether group functionality by reaction of the glycidyl groups with an alkoxide.

6. The method of claim 5, wherein an amount of the enzyme stabilizer in the adding is 0.5-20 wt % with respect to the lignocellulosic biomass.

7. The method of claim 5,
wherein the microorganism capable of producing a saccharifying enzyme is of a strain of aerobic genus *Trichoderma, Aspergillus, Humicola, Irpex* or *Acremonium*.

8. The method claim 5, wherein the enzyme stabilizer comprises a lignin derivative obtained by a process comprising reacting, as a starting material, a lignin in an alkaline waste solution recovered after alkaline cooking.

9. The method of claim 5, wherein the lignin is kraft lignin, lignin acetate, organosolv lignin, steam explosion lignin, lignin sulfate, or alkaline lignin.

10. The method of claim 5, wherein the alkoxide is a methoxide or an ethoxide.

* * * * *